United States Patent [19]

Holmes

[11] Patent Number: 4,793,483

[45] Date of Patent: Dec. 27, 1988

[54] TRAY FOR SURGICAL PATTIES

[76] Inventor: June S. Holmes, 4113 Devonshire Dr., Moss Point, Miss. 39501

[21] Appl. No.: 186,629

[22] Filed: Apr. 27, 1988

[51] Int. Cl.$^4$ .............................................. B65D 85/24
[52] U.S. Cl. ................................... 206/363; 206/438; 206/210
[58] Field of Search ............. 206/234, 363, 210, 63.5, 206/63.3, 369, 366, 372, 438

[56] References Cited

U.S. PATENT DOCUMENTS

| | | | |
|---|---|---|---|
| 863,036 | 8/1907 | Mieden | 206/234 |
| 2,850,152 | 9/1958 | Marrufo | 206/234 |
| 3,861,521 | 1/1975 | Buntz | 206/363 |
| 4,288,066 | 9/1981 | Treacg | 206/210 |
| 4,342,390 | 8/1982 | Mitchell et al. | 206/363 |
| 4,467,946 | 8/1984 | Brown | 206/234 |
| 4,523,679 | 6/1985 | Paikoff et al. | 206/363 |
| 4,637,513 | 1/1987 | Eldrige, Jr. | 206/363 |

*Primary Examiner*—Joseph Man-Fu Moy
*Attorney, Agent, or Firm*—Alexander F. Norcross

[57] ABSTRACT

A tray for surgical patties is a sterilizable, impervious planar sheet having a first upper surface with provided notches for supporting sterile surgical patties by the strings. A flat base member extends at an angle to the upper section and has a retaining lip parallel to but opposite the first upper section. Non-penetrating fastening such as smooth jawed alligator clips are provided at the upper corners of the tray permitting the tray to be suspended from the surgical drapes immediately adjacent the operating area. Holders on the outer edges of the tray are provided to hold an electric cautery, cutter and forceps. The tray permits the ready identification and removal of individual patties directly by the surgeon during the course of the operation significantly simplifying the surgeon's actions during the intricate operational procedures.

4 Claims, 2 Drawing Sheets

TRAY FOR SURGICAL PATTIES

BACKGROUND OF THE INVENTION

This invention relates to the field of ancillary surgical equipment, specifically apparatus for holding and presenting pre-wetted surgical patties for individual selection and use by a physician during the course of an operation.

Surgical sponges are typically provided as pre-sterilized packs of patties of appropriate sizes, each of which has an attached cord for selection, removal, and manipulation of the patty. Such patties are typically packed as multiple units of patties of varying sizes on squares of cardboard or similar material; the individual string may be separated into individual notches for ease of identification and selection of a specific patty. The entire unit is sterilized and pre-wrapped. The disadvantage of this pack is that the patties must normally be used in a moistened state and such pre-moistening tends to damage the container.

Thus, U.S. Pat. No. 4,494,653 to Praderio discloses a container for a plurality of patties having individual count slots for placement of each of the strings attached to the patties. The patties themselves are mounted into recesses for the introduction of wetting fluid.

Much of the effort in providing trays for patties is concentrated on the requirement that patties be counted and accounted for to insure removal from the patient's body before the surgical incision is closed. Thus, U.S. Pat. No. 3,948,390 to Ferreri discloses an enclosed tray for containing patties having therein a vertically mounted card with provided numbered slits for holding individual patty strings to provide a count.

U.S. Pat. No. 4,361,231 to Patience discloses a patty collection device having a multiplicity of pockets in which a specific number of patties may be placed to provide a visual count. A related concept is shown in U.S. Pat. No. 4,637,513 to Eldridge in which an implement collector is shown having a series of provided soft ridges with slits, each numbered for the placement of used surgical needles and the like.

U.S. Pat. No. 4,190,153 to Olsen shows a patty disposal tray in which individual cups, accessible through slits in an otherwise encovering top sheet, may be used for the placement of individual patties.

U.S. Pat. No. 4,312,447 to McWilliams discloses a tray for placement upon a disposal bucket, having notches for the draping of used patties so the exact number of patties that have been disposed of may be known.

U.S. Pat. No. 4,429,789 to Puckett discloses a patty counter in which an accordion folded series of open topped plastic bags are provided within an overall flexible cardboard holder so that they can be opened and hung from the side of a disposal bucket or kick bucket, each used for the receipt of a fixed number of patties.

Finally, U.S. Pat. No. 4,478,332 discloses a patty holder bag again with individual notches for each of the patty cords in which the patties are weighed to determine the number of patties received and disposed of.

SUMMARY OF THE INVENTION

None of the foregoing devices for handling patties provides a ready method for access to a plurality of different sized pre-moistened patties for a physician at the operating site during detailed and meticulous surgery, such a neurosurgery, in which speed and precision of action are essential. Thus, the prior art devices would require that a patty nurse select and place a patty within a surgical instrument, and hand the same to the operating surgeon positioned over the operating site on the patient. Such actions are susceptible to droppage of the patty or contamination of the patty. It is extremely awkward when the surgeon is using the more modern surgeon-held electrical devices; the need for preciseness of feel mandates that the surgeon not let go of the device especially when the device itself is capable of grasping, holding and placing a patty.

Further, pre-wetted surgical patties are relatively slippery. If they slide off their container onto the surgical field, they are contaminated and cannot be used. It is therefore desirable to have some method of retaining the patty within a sterile container during the process of selection and removal and lessening the risk of contamination to the patty during the process of separating a single patty from the multiple pack.

Since the patties need to be moistened with sterile fluid during the course of the operation, it is essential that any container be capable of maintaining the patties in a moistened, but not a saturated state. Thus, it is necessary that there be some drainage for the patties but that the moistening process not damage the container.

The above and foregoing have been provided by the current invention which is of a surgical patty presentation tray. The tray is made out of impervious material, either autoclavable, such as stainless steel, or disposable, such as a pre-sterilizable plastic. In each of the upper two corners of the tray are provided non-penetrating clips for fastening the tray to the surgical drape immediately adjacent to the surgical operating area and a position convenient to both the nurse and the surgeon. The tray is provided at its upper end with series of notches within which are placed the strings for pre-moistened packs of varying sized patties. These patties lie against an angled upper edge of the tray. Below the patties the tray extends out a distance at an acute angle forming a flat base so that any patty which may be removed but is inadvertently dropped will fall onto the base. It then still remains in a sterile area of the tray, and is not contaminated. At the far end of the base an upward retaining lip prevents the patties from sliding off the base of the tray. The tray itself is not an enclosed tray so as to prevent the collection of a moistening fluid; it rather permits the wetting and draining of the patties so that they will be moistened but not saturated.

The tray additionally provides a plurality of vertical tubes for convenient placement by the surgeon of such tools as an electric cauterizer or forceps which would be used concurrently or interchangeably with the removal and placement of the patties during the surgical process in neurosurgery.

It is thus an object of this invention to provide a patty tray which presents a plurality of pre-moistened patties immediately at hand to the surgeon during the operating procedure.

It is a further object of this invention to provide a tray which may be removably affixed to the surgical drapes immediately adjacent the operating area without breaching the sterile field.

It is a further object of this invention to provide a sterilizable surgical patty tray which will hold and present for use a plurality of packs of different sized surgical patties.

It is a further object of this invention to provide a surgical patty tray which will maintain pre-moistened surgical patties in a moistened but not a saturated state.

It is a further object of this invention to provide a surgical patty tray which will tend to retain inadvertently dropped patties, reducing loss and risk of contamination.

These and other objects of the invention may be more clearly seen in the detailed description of the preferred embodiment which follows.

DETAILED DESCRIPTION OF THE PREFERRED EMBODIMENT

Figure 1:
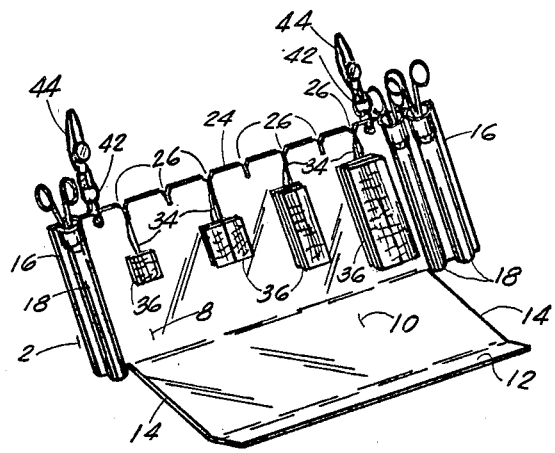
FIG. 1 is a view of the invention showing the placement of various sized patties.
Figure 2:
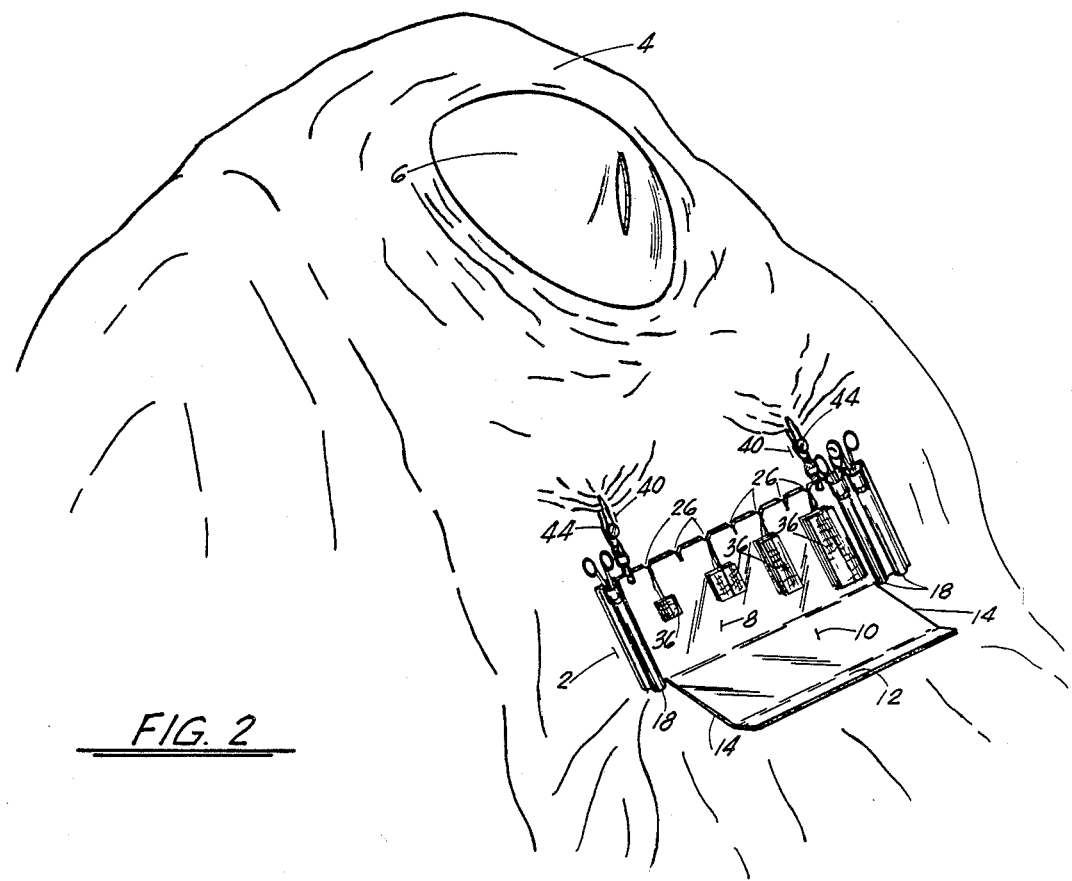
FIG. 2 is a view of the invention as clipped to the surgical drapes adjacent an operating site.
Figure 3:
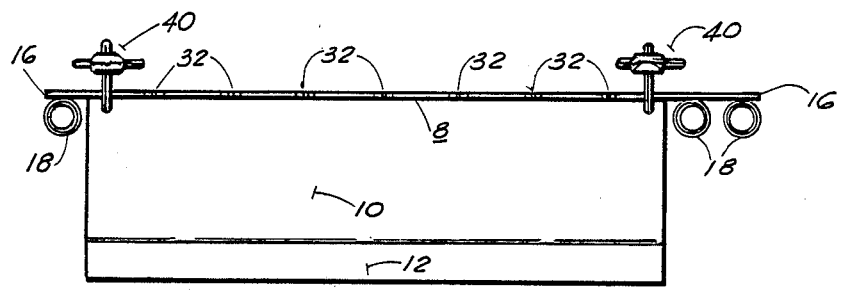
FIG. 3 is a top view of the invention.
Figure 4:
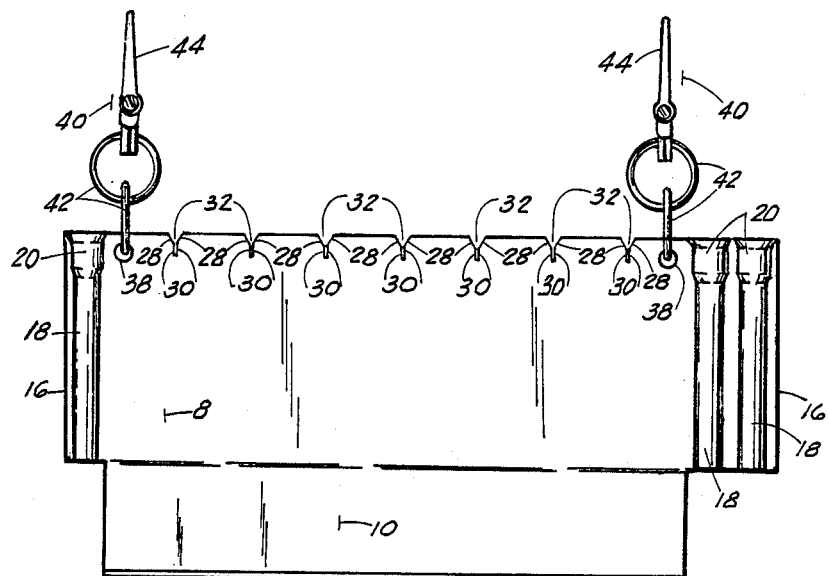
FIG. 4 is a front view of the invention.
Figure 5:
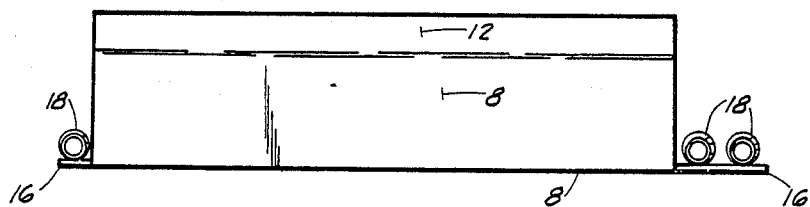
FIG. 5 is a bottom view of the invention.
Figure 6:
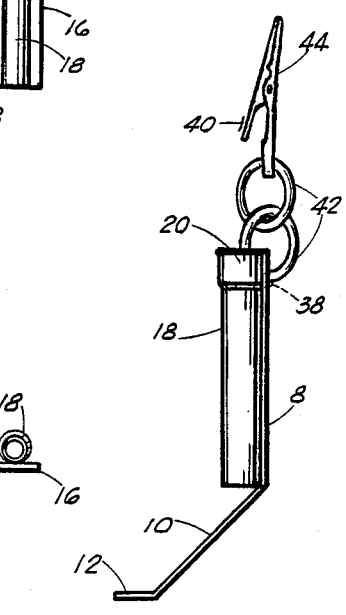
FIG. 6 is a side view of the invention.

FIG. 1 shows the patty tray 2 of the invention; FIG. 2 shows the tray 2 as fastened on a surgical drape proximate to an operating area 6.

Referring to FIG. 1, in conjunction with FIGS. 3 through 6, tray 2 can be seen to comprise an upper, planar patty holder and presentation sheet or plate 8 which is smoothly joined along a bottom line fold at an acute angle to an extended base section 10. Base section 10, in turn, has an upturned retention lip 12 parallel to, but on an opposite side from, upper plate 8.

Base sides 14 are open, not turned up.

Upper plate 8 extends at its lateral ends 16 beyond the base width of base section 10. Vertically arising, and affixed to lateral ends 16, are found operating instrument holders 18, which are open mouthed, open based cylindrical tubes having a slightly widened receiving neck section 20.

At and along upper edge 24 of upper plate 8 are found a plurality of inward extensions 26 which comprise, first, a pair of symmetrical inwardly facing neck edges 28 each of which necks down and connects to string notch edges 30, forming overall string holding grooves 32. Neck edges 28 and notch edges 30 are smoothed so as to provide neither a cutting nor a catching edge. Within various of the string holding grooves 32 are inserted patty strings 34 which in turn hold packs of varying sized surgical patties 36.

Each such surgical patty 36 is, as is well known, a gauze patty, affixed to a string, ending typically in a ring member (not shown) and delivered in packs of multiple patties, each of a uniform size for removal and use as needed by the operating surgeon.

At two opposed outer end points 38 along upper edge 28, proximate to operating instrument holders 18 are attached securing means 40 adapting to secure tray 2 to a surgical drape 4, and from which tray 2 will hang at an angled vertical posture. It is critical that any attachment means *not* penetrate the drapes in order to preserve the sterility of the surgical field. In the preferred embodiment shown, securing means 40 comprise at least two interlocking ring members 42 which secure, in turn, the upper edge of tray 2 to smooth jawed, non-penetrating spring clips 44, which clips, in turn, securely grasp and fasten to surgical drape 4.

Tray 2 is constructed of a non-porous material, either an impervious, autoclavable material, such as stainless steel for a reusable tray or alternatively of an impervious and liquid resistant plastic such as the polyacrylimides for a one time disposable usage.

In use, a sterilized tray 2 is loaded with a selection of patties 36 as are typically provided in a surgical pack for a given operation. Each size patty is separated by a associating the carrier strings for a given size patty pack with a single patty holding groove 32. The tray then, still sterile, is clipped to the surgical drapes next to the prepared and scrubbed operating area 6 so as to hold the tray in an accessible manner to both the surgeon and the assisting nurse. Surgical instruments which must be readily accessible to the surgeon, such as an electric cauterizer, or an electric cutter may be placed and held within the operating instrument holders 18. It has been found to be effective to have at least three such instrument holders 18 for the purposes of holding, readily accessible to the surgeon, a patty forceps, an electric cauterizer, and a cutter; this permits a quick and expedient one or two handed operation directly by the surgeon in utilizing the cutter, the cauterizer, and the patty.

The patties may be spray moistened and will remain moist upon the tray. During the intense activities during an operation it is found that occasionally a patty will be dropped or mishandled in the course of attempting to separate or pick up one patty from a pack.

In the particular tray these patties will slide to the base member but retained from going further by the retention lip and may be readily easily retrieved without loss of sterility.

The entire invention provides convenience at hand to both the nurse and to the operating surgeon, through a unitary device for holding and presenting pre-moistened surgical patties in readily sorted sizes together with the immediate surgical instruments acquired during precision neurological operations, without requiring the repeated passage of tool and patty between nurse and doctor. The surgical patties are easily displayed and can readily be kept moist without over-saturation. The tray placement can be varied to match any patient position since the tray is easily attached to the drapes on the operating table using flexible non-penetrating clips. By providing instrument holders for cauteries, forceps or other instruments immediately at hand to the neurosurgeon, the neurosurgeon's task is significantly eased.

While the above describes a preferred embodiment of the invention, it should be apparent that the invention extends to that wider range of equivalents as are inherent in the claims.

I claim:

1. A tray for surgical patties comprising:
    a. an impervious, autoclavable planar sheet having a first upper section extending from an upper edge to a fold;
    b. said edge having a plurality of inward, V-shaped extensions;
    c. each said extension defining a notch having a wider throat and a narrower base;
    d. each said extension having substantially smooth edges;
    e. a second planar base section extending outward from the fold at an acute angle to the first section, having a length adapted to the length of a typical provided surgical patty;
    f. a retention lip arising at a substantial acute angle from the base section distal the first section; and g. non-penetrating means, at a first and a second upper corner of the first section for fastening the tray to a surgical drape proximate the operating area.

2. A tray as described in claim 2 above further comprising:
   a. a plurality of open ended tubes vertically affixed to the first section at the extreme lateral ends thereof.

3. A tray for surgical patties comprising:
   a. an impervious, disposable planar sheet having a first upper section extending from an upper edge to a fold;
   b. said edge having a plurality of inward, V-shaped extensions;
   c. each said extension defining a notch having a wider throat and a narrower base;
   d. each said extension having substantially smooth edges;
   e. a second planar base section extending outward from the fold at an acute angle to the first section, having a length adapted to the length of a typical provided surgical patty;
   f. a retention lip arising at a substantial acute angle from the base section distal the first section; and
   g. non-penetrating means, at a first and a second upper corner of the first section for fastening the tray to a surgical drape proximate the operating area.

4. A tray as described in claim 3 above further comprising:
   a. a plurality of open ended tubes vertically affixed to the first section at the extreme lateral ends thereof.

* * * * *